United States Patent [19]

Nakao et al.

[11] Patent Number: 4,849,421
[45] Date of Patent: Jul. 18, 1989

[54] ANTI-ANXIETY BENZOTHIEPINO(5,4-C]PYRIDAZINES

[75] Inventors: Toru Nakao, Oita; Minoru Kawakami, Fukuoka; Minoru Obata; Kenji Morita, both of Oita, all of Japan

[73] Assignee: Yoshitomi Pharmaceutical Industries, Ltd., Osaka, Japan

[21] Appl. No.: 162,935

[22] Filed: Mar. 2, 1988

[30] Foreign Application Priority Data

Mar. 2, 1987 [JP] Japan ................................. 62-48497
Jul. 9, 1987 [JP] Japan ................................. 62-172469
Dec. 2, 1987 [JP] Japan ................................. 62-306227

[51] Int. Cl.$^4$ ..................... A61K 31/50; C07D 495/04
[52] U.S. Cl. ..................................... 514/248; 544/234
[58] Field of Search ........................ 544/234; 514/248

[56] References Cited

U.S. PATENT DOCUMENTS

| 3,464,988 | 9/1969 | Holava et al. | 544/234 |
| 3,816,438 | 6/1974 | Houlihan | 546/271 |
| 4,602,019 | 7/1986 | Sircar et al. | 544/234 |
| 4,692,447 | 9/1987 | Cignarella et al. | 544/234 |

FOREIGN PATENT DOCUMENTS

| 0124314 | 11/1984 | European Pat. Off. | 514/248 |
| 0169443 | 1/1986 | European Pat. Off. | 514/248 |
| 8601506 | 3/1986 | World Int. Prop. O. | 544/234 |

OTHER PUBLICATIONS

W. Curran, et al., *Journal of Medicinal Chemistry*, 1974, vol. 17, No. 3, pp. 273–281.
C. Cignarella et al., *Il Farmaco Ed. Sc.* 37(2) pp. 133–144 (1981).
T. Yamada, et al., *Journal of Medicinal Chemistry*, 1982, vol. 25, No. 8, pp. 975–982.

Derwent Abstract 86-015597/03 of EPA Application No. 168350 A, 1/15/86.
J. Lombardino, et al., *Journal of Medicinal Chemistry*, 1981, vol. 24, pp. 830–834.
M. Ali, et al., *Journal Fur Praktische Chemie*, vol. 316, No. 2, 1974, pp. 259–266.

*Primary Examiner*—Richard A. Schwartz
*Attorney, Agent, or Firm*—Sughrue, Mion, Zinn, Macpeak, and Seas

[57] ABSTRACT

A benzothiepino 5,4-c]pyridazine compound of the formula:

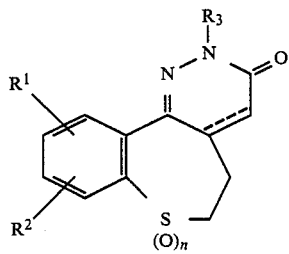

wherein $R^1$ and $R^2$ are the same or different and each is hydrogen, halogen, trifluoromethyl, hydroxy, amino, nitro, cyano, $C_{1-4}$ alkyl, $C_{1-4}$ alkoxy, or $C_{2-5}$ alkanoylamino, $R^3$ is hydrogen, $C_{1-8}$ alkyl, hydroxy-$C_{1-4}$ alkyl, $C_{2-5}$ alkanoyloxy-$C_{1-4}$ alkyl, aryl, aryl-$C_{1-4}$ alkyl, heteroaryl, or substituted aryl, aryl-$C_{1-4}$ alkyl or heteroaryl by 1 to 3 substituents selected from the group consisting of halogen, trifluoromethyl, hydroxy, amino, nitro, cyano, $C_{1-4}$ alkyl, $C_{1-4}$ alkoxy and $C_{2-5}$ alkanoylamino on the armoatic ring, n is 0, 1 or 2, and the bond $===$ between the 4-position and the 4a-position is single bond or double bond. Said compounds exhibit anti-anxietic activity and are useful as anti-anxiety agent.

3 Claims, No Drawings

ANTI-ANXIETY BENZOTHIEPINO(5,4-C]PYRIDAZINES

BACKGROUND OF THE INVENTION

Benzodiazepine compounds such as diazepam have been used as anti-anxiety drugs for the improvement or treatment of symptoms such as anxiety or tention and the like in neuroses, despression or various diseases. However, these benzodiazepine compounds exhibit unfavarable pharmacological effects such as sedative effect, muscle-relaxant effect, anticonvulsant effect, potentiation of alcoholic effect or potentiation of narcotic effect so that such side effects as drowsiness, dizziness or lowering of attentiveness, concentration or reflex movement-ability have become troublesome problems.

Hence, the developments of more selective anti-anxiety drugs with less or no adverse effects have been desired.

In such investigations of anti-anxiety drugs, non-benzodiazepine compounds having affinity for the benzodiazepine receptor in the brain (e.g., European Patent Application No. 168350 A) are provided. But, the known non-benzodiazepine compounds still have matters to be solved such as insufficient selectivity of anti-anxiety effects or lower safety.

It is known that fuzed pyridazine compounds possess various pharmacological effects. In particular, PCT application under W086/01506 discloses benzo[h]cinnoline compounds such as 9-chloro-2-phenyl-4,4a,5,6-tetrahydrobenzo[h]cinnolin-3(2H)-one which have affinity for the benzodiazepine receptor and exhibit anti-anxiety activity. European Patent Application No. 124314 A and U.S. Pat. No. 4,602,019 specifications indicate, for example, 2,4,4a,5-tetrahydro-7-(1H-imidazol1-yl)-3H-indeno[1,2-a]pyridazin-3-one having cardiotonic and antihypertensive activities. Further, European Patent Application No. 169443 A and U.S. Pat. No. 4,692,447 specifications disclose hypotensive, vasodilating, anti-aggressive, anti-thrombotic and cytoprotective[6,7]-benzocycloheptene-[1,2-c]-pyridazin-3-one compounds represented by, for example, 2-n-butyl-2,4,4a,5,6,7-hexahydro-3H-[6,7]-cyclohepten-[1,2-c]-pyridazin-3-one-8-amino.

SUMMARY OF THE INVENTION

The present inventors have made intensive investigations in order to develop non-benzodiazepine compounds with highly selective anti-anxiety activity as well as high safety. According to such investigations, the present inventors have found that novel benzothiepino[5,4-c]pyridazine compounds exhibit potent and selective anti-anxiety activity and very low toxicity.

DETAILED DESCRIPTION

The present invention relates to benzothiepino[5,4-c]pyridazine compounds of the formula:

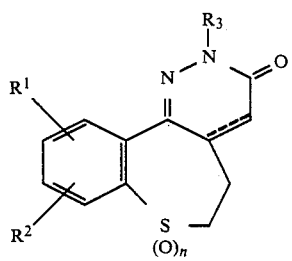

wherein $R^1$ and $R^2$ are the same or different and each is hydrogen, halogen, trifluoromethyl, hydroxy, amino, nitro, cyano, $C_{1-4}$ alkyl, $C_{1-4}$ alkoxy, or $C_{2-5}$ alkanoylamino, $R^3$ is hydrogen, $C_{1-8}$ alkyl, hydroxy-$C_{1-4}$ alkyl, $C_{2-5}$ alkanoyloxy-$C_{1-4}$ alkyl, aryl, aryl-$C_{1-4}$ alkyl, heteroaryl, or substituted aryl, aryl-$C_{1-4}$ alkyl or heteroaryl by 1 to 3 substituents selected from the group consisting of halogen, trifluoromethyl, hydroxy, amino, nitro, cyano, $C_{1-4}$ alkyl, $C_{1-4}$ alkoxy and $C_{2-5}$ alkanoylamino on the aromatic ring, n is 0, 1 or 2, and the bond ═══ between the 4-position and the 4a-position is single bond or double bond; and also relates to uses of said compounds.

In explaining the each symbol of the formula (I) in accordance with the definitions, halogen includes fluorine, chlorine, bromine and iodine; $C_{1-4}$ alkyl includes, for example, methyl, ethyl, propyl, isopropyl, butyl, isobutyl and tert-butyl; $C_{1-4}$ alkoxy includes, for example, methoxy, ethoxy, propoxy, isopropoxy, butoxy, isobutoxy and tert-butoxy; $C_{2-5}$ alkanoylamino includes, for example, acetylamino, propionylamino, butyrylamino and pivaloylamino; hydroxy-$C_{1-4}$ alkyl includes, for example, hydroxymethyl, hydroxyethyl, hydroxypropyl and hydroxybutyl; $C_{2-5}$ alkanoyloxy-$C_{1-4}$ alkyl includes, for example, acetoxymethyl, acetoxyethyl, acetoxypropyl, acetoxybutyl, propionyloxymethyl, propionyloxyethyl, propionyloxypropyl and propionyloxybutyl; $C_{1-8}$ alkyl means straight or branched chain alkyl and includes, for example, methyl, ethyl, propyl, isopropyl, butyl, sec-butyl, tert-butyl, pentyl, isopentyl, neopentyl, hexyl, heptyl, octyl and 2-ethylhexyl; aryl-$C_{1-4}$ alkyl includes, for example, benzyl, phenylethyl, phenylpropyl phenylbutyl, naphthylmethyl, napthylethyl, naphthylpropyl and napthylbutyl; and aryl includes, for example, phenyl and naphthyl; heteroaryl includes, for example, 2-pyridyl, 3-pyridyl, 4-pyridyl, 2-thienyl, 3-thienyl, 2-furyl and 3-furyl; substituted aryl, aryl-$C_{1-4}$ alkyl or heteroaryl by 1 to 3 substituents selected from the group consisting of halogen, trifluoromethyl, hydroxy, amino, nitro, cyano, $C_{1-4}$ alkyl, $C_{1-4}$ alkoxy and $C_{2-5}$ alkanoylamino on the aromatic ring includes, for example, 2-chlorophenyl, 3-chlorophenyl, 4-chlorophenyl, 3,4-dichlorophenyl, 4-bromophenyl, 4fluorophenyl, 3-trifluoromethylphenyl, 4-hydroxyphenyl, 4-aminophenyl, 4-cyanophenyl, 4-methylphenyl, 4-methoxyphenyl, 4-acetylaminophenyl, 4-propionylaminophenyl, 3,4,5-trimethoxyphenyl, 4-chlorobenzyl, 4-methylbenzyl, 2,3-dichlorobenzyl, 4-methoxybenzyl, 4-hydroxybenzyl, 3,4,5-trimethoxybenzyl, 2-(4-chlorophenyl)ethyl, 4-(4-chlorophenyl)butyl, 5-chloro-2-pyridyl, 4,5-dichloro-2-pyridyl, 5-methyl-2-thienyl, 5-methyl-3-thienyl, 5-chloro-2-thienyl and 5-chloro-2-furyl, and the term "aryl", "aryl-$C_{1-4}$ alkyl" and "heteroaryl" in the substituted aryl, aryl-$C_{1-4}$ alkyl or heteroaryl is the same meanings as defined above.

The compounds of the formula (I) having a chiral carbon atom can be prepared as a racemate or an optically active isomer, and the compound (I) having at least two chiral atoms can be obtained as an individual diastereomer or a mixture thereof. The present invention also embraces the mixture thereof and the individual isomers. Furthermore, the present invention embraces stereomers, too.

Preferable compounds of the present invention are 2-(4-chlorophenyl)-5,6-dihydro-[1]benzothiepino[5,4-c]-pyridazin-3(2H)-one, 10-chloro- 2-(4-chlorophenyl)-5,6- dihydro[1]benzothiepino[5,4-c]pyridazin-3(2H)-one 7-oxide, 2-(4-chlorophenyl)-5,6-dihydro-[1]benzothiepino[5,4-c]pyridazin-3(2H)-one 7-oxide, 2-(4-chlorophenyl)-4,4a,5,6-tetrahydro-[1]benzothiepino[5,4-c]pyridazin-3(2H)-one 7-oxide, 2-(4-chlorophenyl)-10-fluoro-5,6-dihydro-[1]benzothiepino[5,4-c]pyridazin-3(2H)-one, 2-(4-chlorophenyl)-10-fluoro-5,6-dihydro-[1]benzothiepino[5,4c]pyridazin-3(2H)-one 7-oxide, 2-(4-bromophenyl)-5,6-dihydro-[1]benzothiepino[5,4-c]pyridazin-3(2H)-one 7-oxide, 2-(4-bromophenyl)-4,4a,5,6-tetrahydro-[1]benzothiepino[5,4-c]pyridazin-3(2H)-one 7-oxide, 10-fluoro-2-(4-fluorophenyl)-5,6-dihydro-[1]benzothiepino[5,4-c]pyridazin-3(2H)-one, 8-chloro-2-(4-chlorophenyl)-5,6-dihydro-[1]benzothiepino[5,4-c]pyridazin-3(2H)-one 7-oxide and 10-fluoro-2-(4-fluorophenyl)-5,6-dihydro-[1]benzothiepino[5,4-c]pyridazin-3(2H)-one 7-oxide.

The present invention also relates to pharmaceutical uses of the benzothiepino[5,4-c]pyridazine compounds of formula (I). Namely, it is provided pharmaceutical composition comprising the compounds of formula (I).

The compounds of formula (I) of the present invention can be, for example, prepared by the methods described as follows.

Method (i)

A method which comprises reacting a compound of the formula:

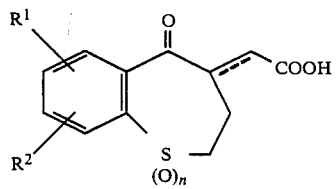
(II)

wherein each symbol is as defind above, with hydrazine derivative of the formula:

$R^3$-NHNH$_2$         (III)

wherein $R^3$ is as defined above, hydrate thereof or an acid addition salt thereof, and then subjecting thus obtained compound of the formula:

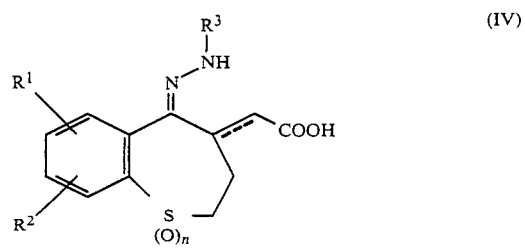

wherein each symbol is as defined above, to a ring closure reaction.

The reaction is carried out by refluxing under heating for 5 to 20 hours in a suitable solvent, for example, in an alcoholic solvent such as methanol, ethanol or propanol to produce the compounds of formulae (I) and (IV).

When the hydrazine derivative of formula (III) is used in the form of the acid addition salt thereof, the above reaction is carried out in the presence of an acid scavenger (e.g., sodium acetate, potassium acetate, sodium hydrogencarbonate, sodium carbonate or potassium carbonate). The compound of the formula (IV), when obtained, is refluxed under heating in acetic acid for 5 to 10 hours to give the compound of formula (I).

Method (ii)

A method for preparing a compound of the formula (I) wherein n is 1 or 2, i.e., oxide or dioxide compound, which comprises subjecting a compound of the formula (I) wherein n is 0, to an oxidative reaction.

The reaction is carried out by keeping the reaction system at 10° to 100° C. for 1 to 10 hours in the presence of an oxidizing agent (e.g., peracetic acid, perbenzoic acid, m-chloroperbenzoic acid or sodium hypobromite) in a suitable solvent. Being kept at room temperature for 1 to 5 hours in the presence of hydrogen peroxide in acetic acid as a solvent, the compound (I), wherein n is 1, can be preferentially prepared, while when keeping the reaction system at 30° to 100° C. for 2 to 10 hours, the compound (I) wherein n is 2 can be obtained.

Method (iii)

A method for preparing the compound (I) wherein $R^3$ is $C_{1-8}$ alkyl, hydroxy-$C_{1-4}$ alkyl, $C_{2-5}$ alkanoyloxy-$C_{1-4}$ alkyl, aryl-$C_{1-4}$ alkyl or substituted aryl-$C_{1-4}$ alkyl, by reacting a compound of the formula (I) wherein $R^3$ is hydrogen, with a compound of the formula:

$R^4$—X         (V)

wherein $R^4$ is $C_{1-8}$ alkyl, hydroxy-$C_{1-4}$ alkyl, $C_{2-5}$ alkanoyloxy-$C_{1-4}$ alkyl, aryl-$C_{1-4}$ alkyl or substituted aryl-$C_{1-4}$ alkyl, and X is a reactive atom or group (e.g., halogen such as chlorine or bromine, or methanesulfonyloxy, toluenesulfonyloxy or benzenesulfonyloxy).

The reaction is carried out by keeping at 0° to 50° C. for 1 to 10 hours in the presence of an acid scavenger (e.g., sodium hydride, sodium amide, sodium methoxide, sodium ethoxide, potassium hydroxide or sodium hydroxide) in a suitable solvent such as nonpolar solvent (e.g., benzene, toluene or xylene), or polar solvent (e.g., N,N-dimethylformamide or acetonitrile).

Method (iv)

A compound of the formula (I) wherein the bond between the 4-position and the 4a-position is double bond, can be prepared by adding bromine dropwise to the compound (I) wherein said bond is single bond, in an acetic acid, as described in Journal of Medicinal Chemistry (J. Med. Chem.) vol. 14, p. 262 (1971).

The reaction is preferably carried out by adding 1 to 1.5 times molar quantity of bromine dropwise to said compound in an acetic acid.

The compound of the formula (I) wherein the bond position indicated by dotted line is double bond, can also be prepared by reacting the compound wherein the bond position indicated by dotted line is single bond with sodium m-nitrobenzenesulfonate (Bachmann Method, British Patent No. 1,168,291).

Method (v)

A method which comprises converting the substituents $R^1$, $R^2$ or $R^3$ of the compounds obtained by the foregoing Methods (i) to (iv) into other substituents according to conventional manners of the organic chemical synthesis.

Such methods include, for example, reduction of a nitro group to an amino group; acylation of an amino group with a lower alkanoic acid; and conversion of an amino group into a cyano group (e.g., Sandmeyer reaction or Gattermann reaction).

The compounds (I) of formula as prepared according to one of the above methods can be separated and purified by means of a conventional manner such as recrystallization or column chromatography.

When the obtained product is a racemate, it can be divided into desired optically active isomers by means of a fractional recrystallization of a salt with an optically active acid, or by column chromatography filled with an optically active carrier. Individual diastereomers can be separated by the method such as fractional crystallization or chromatography. Such compounds can also be obtained by using an optically active starting material. Furthermore, the stereomers can be isolated by the method such as recrystallization or column chromatography.

The followings are the compounds encompassed in the scope of the present invention except those described in the working examples. 10-Fluoro-2-(4-methoxyphenyl)-4,4a,5,6-tetrahydro-[1]benzothiepino[5,4-c]pyridazin-3(2H)-one, 8-Chloro-2-(4-methylphenyl)-4,4a,5,6-tetrahydro-[1]benzothiepino[5,4-c]pyridazin-3(2H)-one, 8-chloro-2-(4-chlorophenyl)-4,4a,5,6-tetrahydro-[1]benzothiepino[5,4-c]pyridazin-3(2H)-one, 9-Chloro-2-(4-chlorophenyl)-4,4a,5,6-tetrahydro-[1]benzothiepino[5,4-c]-pyridazin-3(2H)-one, 9-Chloro-2-(4-methylphenyl)-4,4a,5,6-tetrahydro-[1]benzothiepino[5,4-c]pyridazin-3(2H)-one, 2(4-Chlorophenyl)-10-methoxy-4,4a,5,6-tetrahydro-[1]benzothiepino[5,4-c]pyridazin-3(2H)-one, 10-Methoxy-2-(4-chlorophenyl)- 4,4a,5,6-tetrahydro-[1]benzothiepino[5,4c-]pyridazin-3(2H)-one, 10-Hydroxy-2-(4-methylphenyl)-4,4a,5,6-tetrahydro-[1]benzothiepino[5,4-c]pyridazin-3(2H)-one, 10-Nitro-4,4a,5,6-tetrahydro-[1]benzothiepino[5,4-c]pyridazin-3(2)-one, 10-Nitro-2-phenyl-4,4a,5,6-tetrahydro-[1]benzothiepino[5,4-c]pyridazin-3(2H)-one, 10-Amino-4,4a,5,6-tetrahydro-[1]benzothiepino[5,4-c]pyridazin-3(2H)-one, 10-Amino-2-phenyl-4,4a,5,6-tetrahydro-[1]benzothiepino[5,4-c]pyridazin-3(2H)-one, 10-Cyano-4,4a,5,6-tetrahydro-[1]benzothiepino[5,4-c]pyridazin-3(2H)-one, 10-Acetylamino-4,4a,5,6-tetrahydro-[1]benzothiepino[5,4-c]pyridazin-3(2H)-one, 10-Acetylamino-2-phenyl-4,4a,5,6-tetrahydro-[1]benzothiepino[5,4-c]pyridazin-3(2H)-one, 2-(2-Hydroxyethyl)-4,4a,5,6-tetrahydro-[1]benzothiepino[5,4-c]pyridazin-3(2H)-one, 2-(3-Acetoxypropyl)-4,4a,5,6-tetrahydro-[1]benzothiepino[5,4-c]pyridazin-3(2H)-one, 2-(4-Acetoxybutyl)-4,4a,5,6-tetrahydro-[1]benzothiepino[5,4-c]pyridazin-3(2H)-one, 2-Butyl-4,4a,5,6-tetrahydro-[1]benzothiepino[5,4-c]pyridazin-3(2H)-one, 2-Hexyl-4,4a,5,6-tetrahydro-[1]benzothiepino[5,4-c]pyridazin-3(2H)-one, 2-(3-Trifluoromethylphenyl)-4,4a,5,6-tetrahydro-[1]benzothiepino[5,4-c]pyridazin-3(2H)-one, 2-(4-Hydroxyphenyl)-4,4a,5,6-tetrahydro-[1]benzothiepino[5,4-c]pyridazin-3(2H)-one, 2-(4-Nitrophenyl)-4,4a,5,6-tetrahydro-[ 1]benzothiepino[5,4-c]pyridazin-3(2H)-one, 2-(4-Aminophenyl)-4,4a,5,6-tetrahydro-[1]benzothiepino[5,4-c]pyridazin-3(2H)-one, 2-(4-Cyanophenyl)-4,4a,5,6-tetrahydro-[1]benzothiepino[5,4-c]pyridazin-3(2H)-one, 2-(4-Acetylaminophenyl)-4,4a,5,6-tetrahydro-[1]benzothiepino[5,4-c]pyridazin-3(2H)-one, 2-(4-Propionylaminophenyl)-4,4a,5,6-tetrahydro-[1]benzothiepino[5,4-c]pyridazin-3(2H)-one, 2-Benzyl-4,4a,5,6-tetrahydro-[1]benzothiepino[5,4-c]pyridazine-3(2H)-one, 2-(4-Chlorobenzyl)-4,4a,5,6-tetrahydro-[1]benzothiepino[5,4-c]pyridazin-3(2H)-one, 2-(4-Methylbenzyl)-4,4a,5,6-tetrahydro-[1]benzothiepino[5,4-c]pyridazin-3(2H)-one, 2-(2-Phenylethyl)-4,4a,5,6-tetrahydro-[1]benzothiepino[5,4-c]pyridazin-3(2H)-one, 2-(4-Butylphenyl)-4,4a,5,6-tetrahydro-[1]benzothiepino[5,4-c]pyridazin-3(2H)-one, 8,10-Dimethyl-2-phenyl-4,4a,5,6-tetrahydro-[1]benzothiepino[5,4-c]pyridazin-3(2H)-one, 2-(4-Chlorophenyl)-8,10-dimethyl-4,4a,5,6-tetrahydro-[1]benzothiepino[5,4-c]pyridazin-3(2H)-one, 8,10-Dimethyl-4,4a,5,6-tetrahydro-[1]benzothiepino[5,4-c]pyridazin-3(2H)-one, 8,11-Dimethyl-4,4a,5,6-tetrahydro-[1]benzothiepino[5,4-c]pyridazin-3(2H)-one, 8,11-Dimethyl-2-phenyl-4,4a,5,6-tetrahydro-[1]benzothiepino[5,4-c]pyridazin-3(2H)-one, 2-(5-Methyl-2-thienyl)-4,4a,5,6-tetrahydro-[1]benzothiepino[5,4-c]pyridazin-3(2H)-one, 2-(b 5-Methyl-3-thienyl)-4,4a,5,6-tetrahydro-[ 1]benzothiepino[5,4-c]pyridazin-3(2H)-one, 2-(5-Methyl-2-thienyl)-5,6-dihydro-[1]benzothiepino[5,4-c]pyridazin-3(2H)-one, 2-(5-Methyl-3 thienyl)-5,6-dihydro-[1]benzothiepino[5,4-c]pyridazin-3(2H)-one, 2-(5-Methyl-2-thienyl)-5,6-dihydro-[1]benzothiepino[5,4-c]pyridazin-3(2H)-one 7-oxide, 2-(5-Methyl-3-thienyl)-5,6-dihydro-[1]benzothiepino[5,4-c]pyridazin-3(2H)-one 7-oxide, 2-(5-Methyl-2-thienyl)-4,4a,5,6-tetrahydro-[1]benzothiepino[5,4-c]pyridazin-3(2H)-one 7,7-dioxide, 2-(5-Methyl-3-thienyl)-4,4a,5,6-tetrahydro-[1]benzothiepino[5,4-c]pyridazin-3(2H)-one 7,7-dioxide, 2-(5-Methyl-2-thienyl)-5,6-dihydro-[1]benzothiepino[5,4-c]pyridazin-3(2H)-one 7,7-dioxide, and 2-(5-Methyl-3-thienyl)-5,6-dihydro-[1]benzothiepino[5,4-c]pyridazin-3(2H)-one 7,7-dioxide.

The compounds of the formula (II) of the present invention are novel compounds and can be prepared, for example, by adding methyl iodide to the compound of formula:

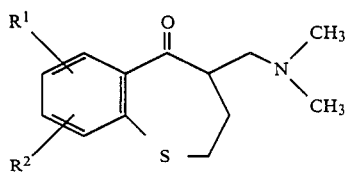

wherein each symbol is as defined above, in acetone; maintaining the mixture at room temperature for 2 to 5 hours to produce a quaternary ammonium compound; adding potassium cyanide or sodium cyanide in methanol or dimethylformamide; stirring at 40°–50° C. for 4 to 8 hours to produce a cyano form of the formula:

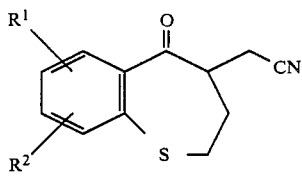

wherein each symbol is as defined above; adding acetic acid and concentrated hydrochloric acid thereto; and maintaining the reaction mixture at 80°–100° C. for 8 to 10 hours to give the compound of formula:

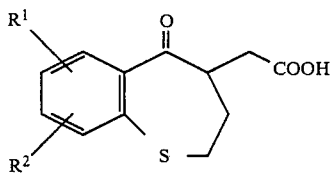

wherein each symbol is as defined above.

For reference, representative compounds of the formula (II') with their physical constants are shown as follows:

5-oxo-2,3,4,5-tetrahydro-[1]benzothiepine-4-acetic acid, melting at 164°–167° C.

7-chloro-5-oxo-2,3,4,5-tetrahydro-[1]benzothiepine-4-acetic acid, melting at 203°–205° C.

7-fluoro-5-oxo-2,3,4,5-tetrahydro-[1]benzothiepine-4-acetic acid, melting at 191°–193° C.

7-methyl-5-oxo-2,3,4,5-tetrahydro-[1]benzothiepine-4-acetic acid, melting at 200°–202° C.

In order to explain the usefulness of the compounds of the present invention, their pharmacological activities together with their experimental methods are shown as follows:

The test compounds employed are as follows:

Compound A: 2-(4-chlorophenyl)-5,6-dihydro-[1]benzothiepino[5,4-c]pyridazin-3(2H)-one Compound B: 10-chloro-2-(4-chlorophenyl)-5,6-dihydro-[1]benzothiepino[5,4-c]pyridazin-3(2H)-one 7-oxide Compound C: 2-(4-chlorophenyl)-5,6-dihydro-[1]benzothiepino[5,4-c]pyridazin-3(2H)-one 7-oxide Compound D: 2-(4-chlorophenyl)-4,4a,5,6-tetrahydro-[1]benzothiepino[5,4-c]pyridazin-3(2H)-one 7-oxide Compound E: 2-(4-chlorophenyl)-10-fluoro-5,6-dihydro[1]benzothiepino[5,4-c]pyridazin-3(2H)-one Compound F: 2-(4-chlorophenyl)-10-fluoro-5,6-dihydro-[1]benzothiepino[5,4-c]pyridazin-3(2H)-one 7-oxide Compound G: 2-(4-bromophenyl)-5,6-dihydro-[1]benzothiepino[5,4-c]pyridazin-3(2H)-one 7-oxide Compound H: 2-(4-bromophenyl)-4,4a,5,6-tetrahydro-[1]benzothiepino[5,4-c]pyridazin-3(2H)-one 7-oxide Compound I: 10-fluoro-2-(4-fluorophenyl)-5,6-dihydro-[1]benzothiepino[5,4-c]pyridazin-3(2H)-one, Compound J: 8-chloro-2-(4-chlorophenyl)-5,6-dihydro-[1]benzothiepino[5,4-c]pyridazin-3(2H)-one 7-oxide Experiment 1: Displacement ability for benzodiazepine receptor:

Experiment on the specific binding for benzodiazepine receptor was performed according to the method described in Life Science, vol. 20, p. 2101 (1977).

A crude synaptosomal fraction was isolated from the cerebral cortex of 9 to 10 week-old male Wistar rats and suspended in 50 mM of Tris-hydrochloric acid buffer solution (pH 7.4) containing 120 mM of sodium chloride and 5 mM of potassium chloride.

To the synaptosomal suspension as prepared above were added various concentrations of test compounds and tritiated diazepam (final concentration: 2 nM), and the mixture was incubated at 0° C. for 20 minutes. Then the suspension was filtered through Whatman GF/B glass fiber filter. After the filter was washed with the foregoing buffer solution, the radioactivity left on the filter was measured by a liquid scintillation spectrometry.

Specific binding was determined by subtracting binding in the presence of 10–6 M unlabelled diazepam from total binding.

The affinity of the test compounds of the present invention for benzodiazepine receptor is evaluated as an ability to displace tritiated diazepam from the binding site, and is represented as Ki value.

The results are summarized in the Table 1.

Experiment 2: Anti-bicuculline effect:

The experiment of anti-bicuculline effect was performed according to the method described in Life Science, vol. 21, p. 1779 (1977).

Groups of 7–14 male ddY-strain mice weighing 20–28 g were used. (+)Bicuculline (0.6 mg/kg) was intravenously administered 1 hour after the oral administration of test compound, and the $ED_{50}$, 50% effective dose, was determined by observing the existence of tonic convulsion within 5 minutes.

The results are summarized in the Table 1.

TABLE 1

| Test compound | Binding for benzodiazepine Ki (nM) | Anti-bicuculline effect ($ED_{50}$, mg/kg p.o.) |
|---|---|---|
| A | 10 | 5.5 |
| B | 11 | 3.2 |
| C | 37 | 1.2 |
| D | 45 | 4.5 |
| E | 14 | 2.2 |
| F | 36 | 0.72 |
| G | 34 | 5.9 |
| H | 44 | 4.5 |
| I | 43 | 6.0 |
| J | 11 | 0.67 |

Experiment 3: Anti-anxiety effect:

The experiment was carried out by using groups of 8 male rats which were maintained at approximately 80% of their free food weights by reducing food and employing a Skinner-box equipped with lever on the side and a grid on the floor.

The rats were placed in the Skinner-box and trained to press a lever in order to obtain milk. According to this training, the rats could obtain 0.1 ml of milk once by pressing the lever twenty times (Fix-ratio 20 reinforcement schedule, $FR_{20}$).

After the rats was trained to obtain milk for 10 minutes according to $FR_{20}$ (this period was hereinafter referred to as unpunished period), loud noise was given to the rats for 5 minutes (this period was hereinafter referred to as punished period). In this punished period, the rats could obtain milk everytime when they pushed the lever once, and also received a foot shock (AC 100V, 0.4–0.8 mA) for 0.3 second through the grid.

According to the repeated training of the unpunished period and the punished period, the animals which continuously pushed the lever in the unpunished period and rarely pushed, it in the punished period, and had the number of shock below 10 were provided to the experiment.

After the rats were orally administered with a test compound in 0.5% methylcellulose, the unpunished period (10 minutes) and the punished period (5 minutes) were alternately performed four times to the rats. The number of push of the lever in the unpunished period in 40 minutes and the number of shock in the punished period in 20 minutes were measured, and minimum effective dose (MED, mg/kg) was determined as the dose which observable the significant increment of number of shock in the punished period with being compared to the control group.

The results are summarized in Table 2.

Experiment 4: Muscle-relaxant effect:

Groups of 10 male mice each were administered orally with test compounds and an hour later placed on the rotating rod (2.8 cm in diameter) turning at a speed of 11 rpm. The $ED_{50}$ (mg/kg) was calculated by the probit method as the dose which caused to drop the half number of mice from the rod within 1 minute. The results are shown in Table 2.

Experiment 5: Potentiation of narcotic effect:

Groups of 14 male mice, which were set in a room kept at 26° C., were administered orally with test compound and an hour later administered intraperitoneally with 40 mg/kg of hexobarbital. The righting reflex was tested at 15 and 30 minutes after hexobarbital treatment. The $ED_{50}$ (mg/kg) was calculated by the probit method as the dose which caused loss of righting reflex for more than 3 seconds in half the mice. The results are shown in Table 2.

Experiment 6: Potentiation of alcoholic effect:

Groups of 14 male mice, which were set in a room kept at 26° C., were administered orally with test compound and an hour later administered intraperitoneally with 0.1 ml/10 g of 30% ethanol. The righting reflex was tested at 15 and 30 minutes after ethanol treatment. The $ED_{50}$ (mg/kg) was calculated by the probit method as the dose which caused loss of righting reflex for more than 3 seconds in half the mice. The results are shown in Table 2.

TABLE 2

| Test Compound | Anti-anxiety effect MED (mg/kg) | Muscle-relaxant effect $ED_{50}$ (mg/kg) | Potentiation of narcotic effect $ED_{50}$ (mg/kg) | Potentiation of alcoholic effect $ED_{50}$ (mg/kg) |
|---|---|---|---|---|
| C | 2.5 | 103 | 113 | 44 |
| F | <5 | 107 | 110 | 117 |
| J | <5 | >500 | >200 | >500 |

All rats survived at 300 mg/kg of intraperitoneal administration and 1000 mg/kg of oral administration of the compounds of the present invention.

According to the various pharmacological experiments inclusive of the above-mentioned experiments, the compounds of formula (I) of the present invention show high affinity for the benzodiazepine receptor, and potent antagonistic effect to the chemical inducer of convulsion such as bicuculline or pentylenetetrazole, and further strong anti-anxiety effect in anti-conflict test using rats. On the contrary, the compounds (I) of the present invention exhibit weak effects in muscular-relaxant effect, potentiation of narcotic effect and potentiation of alcoholic effect, and very low toxicity.

Therefore, the compounds of formula (I) of the present invention are useful as anti-anxiety drugs with high selective activity and high safety, and can be prevent, improve or treat phychosomatic diseases or anxiety neuroses such as autohomic imbalance, nervous vomiting, neurodermatitis, nervous angina or nervous dyspnea, or anxiety or tension induced by various diseases.

The compounds of formula (I) can also be used as neutralizers to an excess dose or a poisoning of the existing anti-anxiety drugs such as diazepam.

Further, a certain group of the compounds (I) possess potentiating effects of phagocytosis of leukocyte or macrophage, and protection effects against infectious diseases, and are useful as potentiator of biological protection. Such effects can be confirmed according to the following pharmacological experiments:

Experiment 7: Activation of peritoneal leukocyte in mice:

Phagocytosis of yeast particles by leukocytes was measured by the modified methods of Stossel et al. (Journal of Clinical Investigation, vol. 51, p. 615, 1972).

Peritoneal leukocytes were obtained from ICR mice (body weight 30–35 g) 3 hours after the intraperitoneal injection of glycogen suspension. After washing leukocytes, the cells were adjusted to $5 \times 10^6$ leukocytes/ml in Hank's solution. A mixture containing 200 $\mu$of the leukocyte suspension, 100 $\mu$of mice serum and 20 $\mu$of the test compound was preincubated at 37° C. for 10 minutes, and then 100 $\mu$l of yeast particles ($1 \times 10^8$/ml) was added. After further incubation of the mixture at 37° C. for 20 minutes, the number of leukocytes phagocytosing more than one yeast particle was counted under a microscope ($\times 400$) up to about 200 leukocytes as a total cell number.

Experiment 8: Activation of peritoneal macrophage in rats:

Peritoneal macrophages were obtained from Wistar rats 3–4 days after the intraperitoneal injection of casein suspension. After washing macrophages, the cells were adjusted to $5 \times 10^6$ macrophages/ml in Hank's solution. Phagocytosis of yeast particles by macrophages was measured in the same procedures as shown in Experiment 7.

Experiment 9: Protection against microbial infection in immunocompromised mice:

Cyclophosphamide (200 mg/kg) was administered intraperitoneally into male ICR mice (5 weeks old) and 1 day later, those mice were injected orally into mice for 3 consecutive days with test compounds at a dose of 3 mg/kg. Each group of mice was inoculated subcutaneously with E. coli 0–111 ($1 \times 10^8$ CFU) 4 days after the cyclophosphamide-treatment. The survival rates of mice were recorded up to 7 days after infection.

The compounds of the present invention, when used as drug, can be administered in the form of tablets, capsules, granules, syrup, injectable solutions, suppositories, powder or the like by mixing with pharmaceutically acceptable additives such as excipient, carrier, diluent and so on. The daily dose, for example, in an oral administration for human adults usually ranges from 5 mg to 500 mg in a single or multiple doses.

Formulation Example

The tablets containing 10 mg of the compound (I) of the present invention can be prepared by the following composition.

| | |
|---|---|
| Compound (I) | 10.0 mg |
| Lactose | 58.5 mg |
| Corn starch | 25.0 mg |
| Crystalline cellulose | 20.0 mg |
| polyvinyl pyrrolidone K-30 | 2.0 mg |
| Talc | 4.0 mg |
| Magnesium stearate | 0.5 mg |
| | 120.0 mg |

Compound (I) is crushed with an atomizer to make a fine powder aving an average particle size below $10\mu$. The fine powder of Compound (I), lactose, corn starch and crystalline cellulose are mixed well in a kneader and then kneaded with a binder prepared by polyvinyl pyrrolidone. The wet mass is passed through a 200 mesh sieve and then dried in an oven at 50° C. The dry granule containing 3–4% of water content is forced through a 24 mesh sieve. Talc and magnesium stearate are mixed and compressed into tablets by using a rotatory tableting machine with a flat punch of 8 mm diameter.

The present invention will be explained by the following examples in more detail, but these examples are not to be construed as limiting the present invention:

EXAMPLE 1

A mixture of 4 g of 5-oxo-2,3,4,5-tetrahydro[1]benzothiepine-4-aceatic acid and 2.0 ml of phenylhydrazine in 50 ml of ethanol is refluxed under heating for 12 hours. After the solvent is distilled off, the mixture of the residue in 20 ml of acetic acid is refluxed under heating for 2 hour. The solvent is distilled off, to the residue is added water and the mixture is extracted with ethyl acetate. The organic layer is washed with water, dried over anhydrous magnesium sulfate and the solvent is distilled off. The crude product is purified by column chromatography and the crystals obtained are recrystallized from ethanol to give 2.3 g of 2-phenyl-4,4a,5,6-tetrahydro-[1]benzothiepino[5,4-c]pyridazin-3(2H)-one, melting at 138°–140° C.

EXAMPLE 2

Substitution in the procedure of Example 1 for the phenylhydrazine used therein of hydrazine produces 4,4a,5,6-tetrahydro-[1]benzothiepino[5,4-c]pyridazin-3(2H)-one, melting at 198°–200° C.

EXAMPLE 3

Substitution in the procedure of Example 1 for the phenylhydrazine used therein of 4-chlorophenylhydrazine produces 2-(4-chlorophenyl)-4,4a,5,6-tetrahydro-[1]benzothiepino[5,4-c]pyridazin-3(2H)-one, melting at 140°–142° C.

EXAMPLE 4

A mixture of 4 g of 5-oxo-2,3,4,5-tetrahydro-[1]benzothiepine-4-acetic acid, 3.5 g of 4-methoxyphenylhydrazine hydrochloride and 1.8 g of sodium acetate in 100 ml of ethanol is refluxed under heating for 12 hours and then the solvent is distilled off. To the residue is added 20 ml of acetic acid and the mixture is refluxed under heating for 2 hours. The solvent is distilled off, and the mixture of the residue in water is extracted with ethyl acetate. The organic layer is washed with water, dried over anhydrous magnesium sulfate and the solvent is distilled off. The crude product obtained is purified by column chromatography and recrystallized from ethanol to give 1.9 g of 2-(4-methoxyphenyl)-4,4a,5,6-tetrahydro-[1]benzothiepino[5,4-c]pyridazin-3(2H)-one, melting at 143°–145° C.

EXAMPLE 5

Substitution in the procedure of Example 4 for the 4-methoxyphenylhydrazine hydrochloride used therein of 4-methylphenylhydrazine hydrochloride produces 2-(4-methylphenyl)-4,4a,5,6-tetrahydro-[1]benzothiepino[5,4-c]pyridazin-3(2H)-one, melting at 128°–130° C.

EXAMPLE 6

Substitution in the procedure of Example 4 for the 4-methoxyphenylhydrazine hydrochloride used therein of 3-chlorophenylhydrazine hydrochloride produces 2-(3-chlorophenyl)-4,4a,5,6-tetrahydro-[1]benzothiepino[5,4-c]pyridazin-3(2H)-one, melting at 122°–123° C.

EXAMPLE 7

Substitution in the procedure of Example 4 for the 4-methoxyphenylhydrazine hydrochloride used therein of 4-bromophenylhydrazine hydrochloride produces 2-(4-bromophenyl)- 4,4a,5,6,-tetrahydro-[1]benzothiepino[5,4-c]pyridazin-3(2H) one, melting at 135°–137° C.

EXAMPLE 8

Substitution in the procedure of Example 4 for the 4-methoxyphenylhydrazine hydrochloride used therein of 2-chlorophenylhydrazine hydrochloride produces 2-(2-chlorophenyl)-4,4a,5,6-tetrahydro-[1]benzothiepino[5,4-c]pyridazin-3(2H)-one, melting at 148°–150° C.

EXAMPLE 9

Substitution in the procedure of Example 4 for the 5-oxo-2,3,4,5-tetrahydro[1]benzothiepine-4-acetic acid used therein of 7-chloro-5-oxo-2,3,4,5-tetrahydro[1]benzothiepine-4-aceatic acid produces 10-chloro-2-(4-methoxyphenyl)-4,4a,5,6-tetrahydro-[1]benzothiepino[5,4-c]pyridazin-3(2H)-one, melting at 159°–161° C.

EXAMPLE 10

Substitution in the procedure of Example 4 for the 5-oxo-2,3,4,5-tetrahydro[1]benzothiepine-4-acetic acid and the 4-methoxyphenylhydrazine hydrochloride used therein of 7-chloro-5-oxo-2,3,4,5-tetrahydro[1]benzothiepine-4-acetic acid and 4-chlorophenylhydrazine hydrochloride, respectively, produces 10 chloro-2-(4-chlorophenyl)-4,4a,5,6-hexahydro-[1]benzothiepino[5,4-c]pyridazin-3(2H)-one, melting at 141°–143° C.

EXAMPLE 11

To a mixture of 3.0 g of 10-chloro-2-(4-chlorophenyl)-4,4a,5,6,-tetrahydro-[1]benzothiepino[5,4-c]pyridazin-3(2H)-one obtained in Example 10 in 90 ml of acetic acid is added 0.4 ml of bromine at 40°–50° C. and stirred for 30 minutes at the same temperature. The mixture is concentrated under reduced pressure and to the residue is added water. The precipitated crystals are collected by filtration, dissolved in chloroform and the solution is washed with water. The organic layer is dried over anhydrous magnesium sulfate and the solvent is distilled off. The crude product obtained is purified by column chromatography and recrystallized from chloroformmethanol to give 2.4 g of 10-chloro-2-(4-chlorophenyl)-5,6-dihydro-[1]benzothiepino[5,4-c]pyridazin-3(2H)-one, melting at 215°–217° C.

EXAMPLE 12

Substitution in the procedure of Example 11 for the 10-chloro-2-(4-chlorophenyl)-4,4a,5,6-tetrahydro-[1]benzothiepino[5,4-c]pyridazin-3(2H)-one used therein of 2-(4-chlorophenyl)-4,4a,5,6-tetrahydro-[1]benzothiepino[5,4-c]pyridazin-3(2H)-one produces 2-(4-chlorophenyl)-5,6-dihydro-[1]benzothiepino[5,4-c]pyridazin-3(2H)-one, melting at 185°–186° C.

EXAMPLE 13

To a mixture of 2.4 g of 10-chloro-2-(4-chlorophenyl)-5,6-dihydro-[1]benzothiepino[5,4-c]pyridazin-3(2H)-one, prepared in Example 11 in 25 ml of water and 300 ml of acetone is added 2.8 g of sodium hypobromite trihydrate. The mixture is stirred for 18 hours at room temperature and concentrated under reduced pressure. To the residue is added water, the precipitated crystals are collected by filtration and recrystallized from dimethylformamide-water to give 1.0 g of 10-chloro-2-(4-chlorophenyl)-5,6-dihydro-[1]benzothiepino[5,4-c]-pyridazin-3(2H)-one 7-oxide, melting at 239°–241° C. with decomposition.

EXAMPLE 14

Substitution in the procedure of Example 13 for the 10-chloro-2-(4-chlorophenyl)-5,6-dihydro-[1]benzothiepino[5,4-c]pyridazin-3(2H)-one used therein of 2-(4-chlorophenyl)-5,6-dihydro-[1]benzothiepino[5,4-c]pyridazin-3(2H)-one prepared in Example 12 produces 2-(4-chlorophenyl)-5,6-dihydro-[1]benzothiepino[5,4-c]pyridazin-3(2H)-one 7-oxide melting at 233°–234° C. with decomposition.

EXAMPLE 15

Substitution in the procedure of Example 13 for the 10-chloro-2-(4-chlorophenyl)-5,6-dihydro[1]benzothiepino[ 5,4-c]pyridazin-3(2H)-one used therein of 2-(4-methoxyphenyl)-4,4a,5,6-tetrahydro-[1]benzothiepino[5,4-c]pyridazin-3(2H)-one prepared in Example 4 produces 2-(4-methoxyphenyl)-4,4a,5,6-tetrahydro-[1]benzothiepino[5,4-c]pyridazin-3(2H)-one 7-oxide, melting at 203°–205° C. with decomposition.

EXAMPLE 16

Substitution in the procedure of Example 13 for the 10-chloro-2-(4-chlorophenyl)-5,6-dihydro[1]benzothiepino[5,4-c]pyridazin-3(2H)-one used therein of 2-phenyl-4,4a,5,6-tetrahydro-[1]benzothiepino[5,4-c]pyridazin-3(2H)-one prepared in Example 1 produces 2-phenyl-4,4a,5,6-tetrahydro-[1]benzothiepino[5,4-c]pyridazin-3(2H)-one 7-oxide, melting at 187°–190° C. with decomposition.

EXAMPLE 17

Substitution in the procedure of Example 13 for the 10-chloro-2-(4-chlorophenyl)-5,6-dihydro-[1]benzothiepino[5,4-c]pyridazin-3(2H)-one used therein of 2-(4-chlorophenyl)-4,4a,5,6-tetrahydro-[1]benzothiepino[5,4-c]pyridazin-3(2H)-one prepared in Example 3 produces 2-(4-chlorophenyl)-4,4a,5,6-tetrahydro-[1]benzothiepino[5,4-c]pyridazin-3(2H)-one 7-oxide, melting at 217°–220° C. with decomposition.

EXAMPLE 18

2-(4-Chlorophenyl)-4,4a,5,6-tetrahydro-[1]benzothiepino[5,4-c]pyridazin-3(2H)-one 7-oxide prepared in Example 17 is separated and purified by column chromatography on silica gel using a mixture of hexane and ethyl acetate (3:1) as an eluent. The crystals obtained from the first fraction of eluate are recrystallized from isopropyl alcohol to give (4aR*, 7S*)-2-(4-chlorophenyl)-4,4a,5,6-tetrahydro-[1]benzothiepino[5,4-c]pyridazin-3(2H)-one 7-oxide, melting at 247°–248° C. with decomposition. And also the crystals obtained from the second fraction of eluate are recrystallized from isopropyl alcohol to give (4aR*, 7R*)-2-(4-chlorophenyl)-4,4a,5,6-tetrahydro-[1]benzothiepino[5,4-c]pyridazin-3(2H)-one 7-oxide, melting at 190°–191° C. with decompostion.

EXAMPLE 19

Substitution in the procedure of Example 13 for the 10-chloro-2-(4-chlorophenyl)-5,6-dihydro-[1]benzothiepino-[5,4-c]pyridazin-3(2H)-one used therein of 10-chloro-2-(4-chlorophenyl)-4,4a,5,6-tetrahydro-[1]benzothiepino[5,4-c]pyridazin-3(2H)-one prepared in Example 10 produces 10-chloro-2-(4-chlorophenyl)-4,4a,5,6-tetrahydro-[1]benzothiepino[5,4-c]pyridazin-3(2H)-one 7-oxide, melting at 198°–202° C. with decompostion.

EXAMPLE 20

To a solution of 14 g of 2-(4-chlorophenyl)-5,6-dihydro-[1]benzothiepino[5,4-c]pyridazin-3(2H)-one 7-oxide prepared in Example 14 in 200 ml of acetic acid is added 15 ml of hydrogen peroxide with stirring at room temperature. The mixture is stirred at 50°–55° C. for 2 hours, poured into 1 liter of water and the precipitated crystals are collected by filtration. The crude products obtained are purified by column chromatography on silica gel and recrystallized from chloroform-methanol to give 9.8 g of 2-(4-chlorophenyl-5,6-dihydro-[1]benzothiepino[5,4-c]pyridazin-3(2H)-one 7,7-dioxide, melting at above 310° C.

EXAMPLE 21

Substitutions in the procedure of Example 1 for the 5-oxo-2,3,4,5-tetrahydro[1]benzothiepine-4-acetic acid and the phenylhydrazine used therein of 7-fluoro-5-oxo-2,3,4,5-tetrahydro[1]benzothiepine-4-acetic acid and 4-chlorophenylhydrazine produces 2-(4-chlorophenyl)-10-fluoro-4,4a,5,6,-tetrahydro-[1]benzothiepino[5,4-c]pyridazin-3(2H)-one, melting at 141°–142° C.

EXAMPLE 22

Substitution in the procedure of Example 11 for the 10-chloro-2-(4-chlorophenyl)-4,4a,5,6-tetrahydro-[1]benzothiepino[5,4-c]pyridazin-3(2H)-one used therein of 2-(4-chlorophenyl)- 10-fluoro-4,4a,5,6-tetrahydro-[1]benzothiepino[5,4-c]pyridazin-3(2H)-one produces 2-(4-chlorophenyl) 10-fluoro-5,6-dihydro-[1]benzothiepino[5,4-c]pyridazin-3(2H)-one, melting at 160°–162° C.

EXAMPLE 23

To a solution of 1.8 g of 2-(4-chlorophenyl)-10-fluoro-5,6-dihydro-[1]benzothiepino[5,4-c]pyridazin-3(2H)one, prepared in Example 22, in 20 ml of acetic acid is added 1.3 ml of 35% hydrogen peroxide with stirring at room temperature and furthermore stirred for 5 hours at the same temperature. To the resultant mixture is added water, and the precipitated crystals are collected by filtration and recrystallized from dimethylformamide-water to give 1.3 g of 2-(4-chlorophenyl)-10-fluoro-5,6-dihydro[1]benzothiepino[5,4-c]pyridazin-3(2H)-one 7-oxide, melting at 233°–235° C. with decomposition.

EXAMPLE 24

To a solution of 8 g of 9-chloro-5-oxo-2,3,4,5-tetrahydro-[1]benzothiepine-4-acetic acid in 100 ml of butanol is added 5 g of 4-chlorophenylhydrazine and the mixture is refluxed under heating for 16 hours. The solvent is distilled off, to the residue is added 20 ml of acetic acid and the mixture is refluxed under heating for 5 hours. The solvent is distilled off, to the residue is added water and the mixture is extracted with ethyl acetate. The organic layer is washed with aqueous sodium hydrogen carbonate, dried over anhydrous magnesium sulfate and the solvent is distilled off. The residue is purified by column chromatography on silica gel to give 3 g of pale brown oil.

To the solution of the oil in 30 ml of acetic acid is added 0.41 ml of bromine at room temperature and stirred at 40°–50° C. for an hour. After the completion of the reaction, the solvent is distilled off under reduced pressure. The residue is purified by column chromatography on silica gel and recrystallized from ethanol to give 8-chloro-2-(4-chlorophenyl)-5,6-dihydro-[1]benzothiepino[5,4-c]pyridazin-3(2H)-one, melting at 166°–168° C.

EXAMPLE 25

To a solution of 0.9 g of 8-chloro-2-(4-chlorophenyl)-5,6-dihydro[1]benzothiepino[5,4-c]pyridazin-3(2H)-one, prepared in Example 24, in 20 ml of acetic acid is added 0.6 ml of 35% hydrogen peroxide with stirring at room temperature and the mixture is stirred for 18 hours at the same temperature. To the residue is added water, and the precipitated crystals are collected by filtration and repeatedly washed with ethanol to give 0.7 g of 8-chloro-2-(4-chlorophenyl)-5,6-dihydro-[1]benzothiepino[5,4-c]pyridazin-3(2H)-one 7-oxide, melting at 217°–219° C. with decomposition.

EXAMPLE 26

To a mixture of 92 g of 4,4a,5,6-tetrahydro[1]benzothiepino[5,4-c]pyridazin-3(2H)-one in 920 ml of acetic acid is added 64 g of bromine dropwise at 50°–60° C., and the mixture is kept at the same temperature for an hour and poured into a large quantity of water. The precipitated crystals are collected by filtration, and washed with warm water and then with ethanol. The crystals are dried to give 85 g of 5,6-dihydro-[1]benzothiepino[5,4-c]pyridazin-3(2H)-one, melting at 311°–313° C. with decomposition.

EXAMPLE 27

To a solution of 5 g of the compound, prepared in Example 26, in 50 ml of dimethylformamide is added 1.0 g of 60% sodium hydride, and the mixture is stirred for 30 minutes. To the mixture is added 5 g of methyl iodide dropwise at 35°–40° C. and kept at the same temperature for an hour. The mixture is poured into water, extracted with ethyl acetate, and the extract is washed with water and dried over magnesium sulfate. The resultant solution is concentrated, and the precipitated crystals are collected by filtration and recrystallized from ethanol to give 2.8 g of 2-methyl-5,6-dihydro-[1]benzothiepino[5,4-c]pyridazin-3(2H)-one, melting at 139°–140° C.

EXAMPLE 28

Substitution in the procedure of Example 27 for the methyl iodide used therein of benzyl chloride produces 2-benzyl-5,6-dihydro-[1]benzothiepino[5,4-c]pyridazin-(32H)-one, melting at 190°–192° C.

EXAMPLE 29

Substitution in the procedure of Example 27 for the methyl iodide used therein of 4-chlorobenzyl chloride produces 2-(4-chlorobenzyl)-5,6-dihydro-[1]benzothiepino[5,4-c]pyridazin-3(2H)-one, melting at 224°–225° C.

EXAMPLE 30

Substitution in the procedure of Example 27 for the methyl iodide used therein of butyl bromide produces 2-butyl-5,6-dihydro-[1]benzothiepino[5,4-c]pyridazin3(2H)-one, melting at 108°–110° C.

EXAMPLE 31

To a solution of 5.8 g of the compound, prepared in Example 28, in 200 ml of acetic acid is added 5 g of 35% hydrogen peroxide and the mixture is kept at a room temperature for 5 hours. The mixture is poured into ice-cold water, and the precipitated crystals are collected by filtration and recrystallized from 60% aqueous acetic acid solution to give 4.2 g of 2-(4-chlorobenzyl)-5,6-dihydro[1]benzothiepino[5,4-c]pyridazin-3(2H)-one 7-oxide, melting at 207°–209° C. with decomposition.

EXAMPLE 32

A mixture of 3.4 g of the compound, prepared in Example 31, in 200 ml of acetic acid is warmed at 45°–50° C. To the mixture is added 20 g of 35% aqueous hydrogen peroxide solution and kept at the same temperature for 3 hours and then poured into a large quantity of water. The precipitated crystals are collected by filtration, washed with water and recrystallized from 60% aqueous acetic acid solution to give 2.6 g of 2-(4-chlorobenzyl)-5,6-dihydro[1]benzothiepino[5,4-c]pyridazin-3(2H)-one 7,7-dioxide, melting at 238°–239° C. with decomposition.

The following compounds can be prepared in a similar manner as the above Examples.

EXAMPLE 33

2-(4-bromophenyl)-5,6-dihydro-[1]benzothiepino[5,4-c]pyridazin-3(2H)-one 7-oxide, melting at 227° C. with decomposition.

EXAMPLE 34

10-methyl-4,4a,5,6-tetrahydro-[1]benzothiepino[5,4-c]pyridazin-3(2H)-one, melting at 185°–187° C.

EXAMPLE 35

2-(4-chlorophenyl)-10-methyl-4,4a,5,6-tetrahydro[1-]benzothiepino[5,4-c]pyridazin-3(2H)-one, melting at 151°–153° C.

EXAMPLE 36

10-methyl-2-(4-methylphenyl)-4,4a,5,6-tetrahydro-[1]benzothiepino[5,4-c]pyridazin-3(2H)-one, melting at 164°–166° C.

EXAMPLE 37

2-(4-bromophenyl)-4,4a,5,6-tetrahydro-[1]benzothiepino[5,4-c]pyridazin-3(2H)-one 7-oxide, melting at 227°–229° C. with decomposition.

EXAMPLE 38

2-(4-bromophenyl)-5,6-dihydro-[1]benzothiepino[5,4-c]pyridazin-3(2H)-one, melting at 199°–201° C.

EXAMPLE 39

2-(4-chlorophenyl)-10-methyl-5,6-dihydro-[1]benzothiepino[5,4-c]pyridazin-3(2H) one, melting at 182°–184° C.

EXAMPLE 40

2-(4-chlorophenyl)-10-methyl-5,6-dihydro-[1]benzothiepino[5,4-c]pyridazin-3(2H)-one 7-oxide, melting at 237°–239° C. with decomposition.

EXAMPLE 41

10-fluoro-2-(4-fluorophenyl)-4,4a,5,6-tetrahydro-[1]benzothiepino[5,4-c]pyridazin-3(2H)-one, melting at 175°–177° C.

EXAMPLE 42

10-fluoro-2-(4-fluorophenyl)-5,6-dihydro-[1]benzothiepino[5,4-c]pyridazin-3(2H)-one, melting at 169°–171° C.

EXAMPLE 43

10-fluoro-2-(4-fluorophenyl)-5,6-dihydro-[1]benzothiepino[5,4-c]pyridazin-3(2H)-one 7-oxide, melting at 227°–229° C. with decomposition.

EXAMPLE 44

2-(4-fluorophenyl)-4,4a,5,6-tetrahydro-[1]benzothiepino[5,4-c]pyridazin-3(2H)-one, melting at 146°–147° C.

EXAMPLE 45

2-(4-fluorophenyl)-5,6-dihydro-[1]benzothiepino[5,4-c]pyridazin-3(2H)-one, melting at 163°–165° C.

EXAMPLE 46

2-(4-fluorophenyl)-5,6-dihydro-[1]benzothiepino[5,4-c]pyridazin-3(2H)-one 7-oxide, melting at 225°–226° C. with decomposition.

EXAMPLE 47

2-(3,4-dichlorophenyl)-4,4a,5,6-tetrahydro-[1]benzothiepino[5,4-c]pyridazin-3(2H)-one, melting at 134°–136° C.

EXAMPLE 48

10-fluoro-2-(3,4-dichlorophenyl)-5,6-dihydro-[1]benzothiepino[5,4-c]pyridazin-3(2H)-one, melting at 156°–157° C.

EXAMPLE 49

10-fluoro-2-(3-trifluoromethylphenyl)-5,6-dihydro[1-]benzothiepino[5,4-c]pyridazin-3(2H)-one 7-oxide, melting at 203°–204° C. with decomposition.

EXAMPLE 50

10-fluoro-2-(3,4-dichlorophenyl)-5,6-dihydro-[1]benzothiepino[5,4-c]pyridazin-3(2H)-one 7,7-dioxide, melting at 253°–255° C. with decomposition.

EXAMPLE 51

8-chloro-2-(4-chlorophenyl)-5,6-dihydro-[1]benzothiepino[5,4-c]pyridazin 3(2H)-one 7,7-dioxide, melting at 219°–220° C. with decomposition.

Although the present invention has been adequately discussed in the foregoing specification and examples included therein, one readily recongnizes that various changes and modifications may be made without departing from the spirit and scope thereof.

What is claimed is:

1. A benzothiepino[5,4-c]pyridazine compound of the formula:

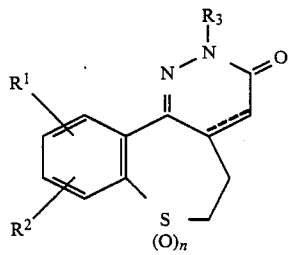

wherein $R^1$ and $R^2$ are the same or different and each is hydrogen, halogen, trifluoromethyl, hydroxy, amino, nitro, cyano, $C_{1-4}$ alkyl, $C_{1-4}$ alkoxy, or $C_{2-5}$ alkanoylamino, $R^3$ is hydrogen, $C_{1-8}$ alkyl, hydroxy-$C_{1-4}$ alkyl, $C_{2-5}$ alkanoyloxy-$C_{1-4}$ alkyl, phenyl, naphthyl, phenyl-$C_{1-4}$ alkyl, nalhthyl-$C_{1-4}$ alkyl, pyridyl, thienyl, furyl, or phenyl, naphthyl, phenyl-$C_{1-4}$ alkyl, naphthyl-$C_{1-4}$ alkyl, pryidyl, thienyl or furyl subsitituted by 1 to 3 subtituents selected from the group consisting of halogen, trifluoromethyl, hydroxy, amino, nitro, cyano, $C_{1-4}$ alkyl, $C_{1-4}$ alkoxy and $C_{2-5}$ alkanoylamino on the aromatic ring, n is 0, 1 or 2, and the bond between the 4-position and the 4a-position is single bond or double bond.

2. A compound of claim 1, wherein said compound is 2-(4-chlorophenyl)-5,6-dihydro-[1]benzothiepino[5,4-c]pyridazin-3(2H)-one, 10-chloro-2-(4-chlorophenyl)-5,6-dihydro-[1]benzothiepino[5,4-c]pyridazin-3(2H)-one 7oxide, 2-(4-chlorophenyl)-5,6-dihydro-[1]benzothiepino[5,4-c]pyridazin-3(2H)-one 7-oxide, 2-(4-chlorophenyl)4,4a,5,6-tetrahydro-[1]benzothiepino[5,4-c]pyridazin-3(2H)-one 7-oxide, 2-(4-chlorophenyl)-10-fluoro-5,6-dihydro-[1]benzothiepino[5,4-c]pyridazin-3(2H)-one, 2-(4-chlorophenyl)-10-fluoro-5,6-dihydro-[1]benzothiepino[5,4c]pyridazin-3(2H)-one 7-oxide, 2-(4-bromophenyl)-5,6-dihydro-[1]benzothiepino[5,4-c]pyridazin-3(2H)-one 7-oxide, 2-(4 bromophenyl)-4,4a,5,6-tetrahydro-[1]benzothiepino[5,4-c]pyridazin-3(2H)-one 7-oxide, 10-fluoro-2-(4-fluorophenyl)-5,6-dihydro-[1]benzothiepino[5,4-c]pyridazin-3(2H)-one, 8-chloro-2-(4-chlorophenyl)-5,6-dihydo-[1]benzothiepino[5,4-c]pyridazin-3(2H)-one 7-oxide or 10-fluoro-2-(4-fluorophenyl)-5,6-dihydro-[1]benzothiepino[5,4-c]pyridazin-3(2H)-one 7-oxide.

3. A pharmaceutical composition comprising a therapeutically effective amount of the compound of claim 1 and a pharmaceutically acceptable additive.

* * * * *